(12) United States Patent
Huang et al.

(10) Patent No.: US 12,121,041 B2
(45) Date of Patent: Oct. 22, 2024

(54) APPLICATIONS OF DIPHENYLPROPENONE COMPOUND IN PREPARING ANIMAL FEED ADDITIVE OR ANIMAL FEED

(71) Applicant: Xianfeng Peng, Guangzhou (CN)

(72) Inventors: Huacheng Huang, Guangzhou (CN); Xianfeng Peng, Guangzhou (CN)

(73) Assignee: Xianfeng Peng, Guangzhou (CN)

( * ) Notice: Subject to any disclaimer, the term of this patent is extended or adjusted under 35 U.S.C. 154(b) by 645 days.

(21) Appl. No.: 17/294,887

(22) PCT Filed: Nov. 19, 2018

(86) PCT No.: PCT/CN2018/116274
§ 371 (c)(1),
(2) Date: May 18, 2021

(87) PCT Pub. No.: WO2020/102952
PCT Pub. Date: May 28, 2020

(65) Prior Publication Data
US 2021/0400997 A1    Dec. 30, 2021

(51) Int. Cl.
*A23K 20/111*    (2016.01)
*A23K 10/30*    (2016.01)

(52) U.S. Cl.
CPC ............ *A23K 20/111* (2016.05); *A23K 10/30* (2016.05)

(58) Field of Classification Search
CPC .................................................... A23K 20/111
See application file for complete search history.

(56) References Cited

U.S. PATENT DOCUMENTS

| | | | |
|---|---|---|---|
| 10,159,265 B2 | 12/2018 | Teres et al. | |
| 2003/0203857 A1 | 10/2003 | Ohnogi et al. | |
| 2007/0092551 A1* | 4/2007 | Enoki ................ | A23K 20/111 |
| | | | 514/688 |
| 2007/0112066 A1 | 5/2007 | Ohnogi et al. | |
| 2009/0239944 A1 | 9/2009 | D'orazio et al. | |
| 2012/0046353 A1 | 2/2012 | Yoon et al. | |
| 2017/0231253 A1 | 8/2017 | Hristov | |

FOREIGN PATENT DOCUMENTS

| | | |
|---|---|---|
| CN | 1436074 A | 8/2003 |
| CN | 1890205 A | 1/2007 |
| CN | 101331913 A | 12/2008 |
| CN | 101703159 A | 5/2010 |
| CN | 104664086 A | 6/2015 |
| CN | 107698492 A | 2/2018 |
| JP | 2008543901 A | 12/2008 |
| JP | 2009073761 A | 4/2009 |
| JP | 2014172893 A | 9/2014 |
| RU | 2576195 C1 | 2/2016 |
| TW | 200509886 A | 3/2005 |
| WO | 2013156574 A1 | 10/2013 |
| WO | 2016014019 A1 | 1/2016 |

OTHER PUBLICATIONS

International Search Report, and English Translation thereof, and Written Opinion for International Application No. PCT/CN2018/116274, mailed Aug. 7, 2019 (12 pages).
He, "Studies on the synthesis and properties of some flavonoids", Chinese Master's Theses Full-text Database, Apr. 30, 2012, (79 pages).
Chinese Office Action and Search Report, and Brief Translation of the Objections thereof, for Chinese Counterpart Application No. 201880011850.8, mailed Jan. 17, 2022 (9 pages).
Russian Office Action, and English Translation thereof, for Russian Counterpart Application No. 2021117251/10, mailed Oct. 26, 2021 (12 pages).
Extended European Search Report for European Counterpart Application No. 18940688.7, mailed Nov. 5, 2021 (8 pages).
Yadav et al., "Synthesis and biological evaluation of anti-inflammatory activity of 1,3 diphenyl propenone derivatives," Medical Chemistry Research, vol. 20, pp. 461-465, Published Online Mar. 21, 2010, (5 pages).
Japanese Office Action, and Brief Translation of the Objections thereof, for Japanese Counterpart Application No. 2021-527858, mailed Aug. 23, 2022 (5 pages).

* cited by examiner

*Primary Examiner* — Jenna A Watts
(74) *Attorney, Agent, or Firm* — Kagan Binder, PLLC

(57) ABSTRACT

Applications of a diphenylpropenone compound of general formula (I), or a stereoisomer thereof, or a geometric isomer thereof, or a tautomer thereof, or a solvate thereof, or a salt acceptable for feed in the preparation of an animal feed additive or animal feed. Confirmed by animal breeding test, the diphenylpropenone compound, or the stereoisomer thereof, or the geometric isomer thereof, or the tautomer thereof, or the solvate thereof, or the salt acceptable for the feed can be used as the animal feed additive or the animal feed. Animal weight can be effectively increased, survival rates can be enhanced, and the compound has a good effect of improving animal production performance.

(I)

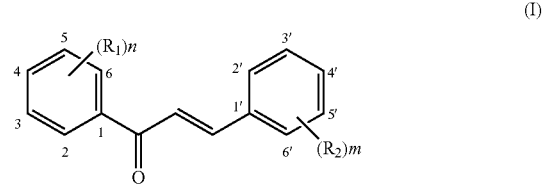

9 Claims, No Drawings

APPLICATIONS OF DIPHENYLPROPENONE COMPOUND IN PREPARING ANIMAL FEED ADDITIVE OR ANIMAL FEED

TECHNICAL FIELD

The present disclosure relates to a technical field of animal feed, in particular to a use of diphenylpropenone compounds in preparation of animal feed additives or animal feeds.

BACKGROUND

Diphenylpropenone compounds are widely distributed in nature and are a kind of important organic intermediate with a wide range of biological activities.

Feed additives refer to small or trace substances added during processing, production, and use of feeds, including nutritive feed additives and general feed additives. General feed additives refer to small or trace amounts of substances mixed into feeds to ensure or improve the feed quality and increase the efficiency of feed utilization. The general feed additives commonly used in this field that can efficiently and stably increase the efficiency of feed utilization and improve the animal production performance mainly include high-level copper agents, high-level zinc agents, feed antibiotics, chemically synthesized antimicrobial agents, etc. However, the long-term use of these substances in the breeding industry has great side effects, such as the disadvantages of liver and kidney toxicity to animals, growth inhibition, kidney function damage, urinary tract disorders, teratogenicity, mutagenesis, the production of drug resistance, drug residues and environmental pollution, or the like. In order to protect the health of animals and improve the production efficiency of the breeding industry, seeking a new effective, stable and safe feed additive, especially a general feed additive, is an urgent problem to be solved in this field.

At present, there is no research to disclose the use of diphenylpropenone compounds in feed additives or feeds.

SUMMARY

Based on this, it is necessary to provide a use of a diphenylpropenone compound in a preparation of animal feed additives.

The present disclosure provides a use of a diphenylpropenone compound represented by General Formula (I), or a stereoisomer, a geometric isomer, a tautomer, a solvate or a feed acceptable salt thereof in a preparation of animal feed additives or animal feeds,

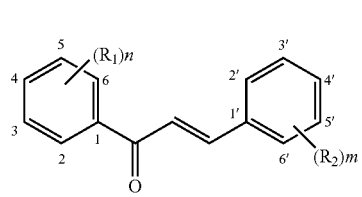

(I)

wherein, $R_1$ is each optionally selected from OH, $C_1$-$C_{20}$ alkyl, $OC_1$-$C_{20}$ alkyl, $C(=O)OH$, $C(=O)OC_1$-$C_{20}$ alkyl or X; $R_2$ is each optionally selected from OH, $C_1$-$C_{20}$ alkyl, $OC_1$-$C_{20}$ alkyl or X; n and m are integers from 0 to 5, and X is F, Cl, Br or I.

In one embodiment, $R_1$ is each optionally selected from OH, $OC_1$-$C_5$ alkyl, $C_1$-$C_5$ alkyl, $C(=O)OH$ or $C(=O)OC_1$-$C_5$ alkyl, F, Cl or Br.

In one embodiment, $R_1$ is each optionally selected from OH, $C(=O)OH$, $OC_1$-$C_5$ alkyl or Cl.

In one embodiment, $R_2$ is each optionally selected from OH, $OC_1$-$C_5$ alkyl, $C_1$-$C_5$ alkyl, F, Cl or Br.

In one embodiment, $R_2$ is each optionally selected from $C_1$-$C_5$ alkyl, $OC_1$-$C_5$ alkyl or Cl.

In one embodiment, n≠0.

In one embodiment, $R_1$ is each optionally selected from OH, $C(=O)OH$, or Cl; $R_2$ is each optionally selected from $C_1$-$C_5$ alkyl or Cl.

In one embodiment, the diphenylpropenone compound is selected from the group consisting of the following compounds:

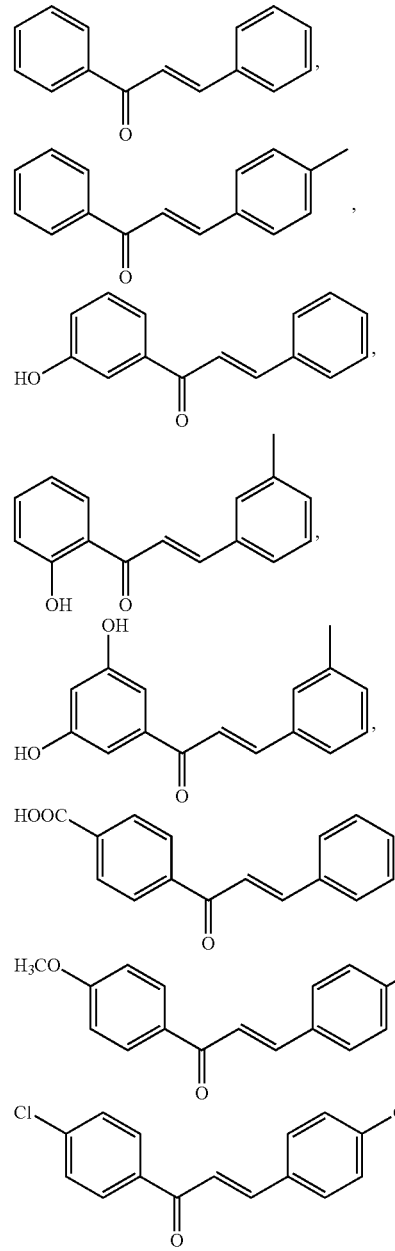

-continued

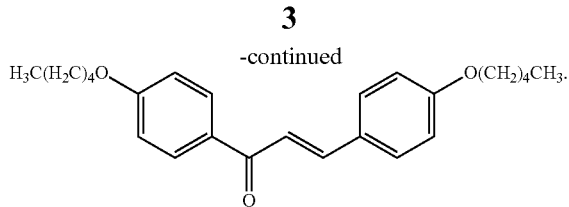

The present disclosure further provides a feed composition comprising the diphenylpropenone compound represented by General Formula (I), or the stereoisomer, the geometric isomer, the tautomer, the solvate or the feed acceptable salt thereof in the above use, and one or more of a feedable accessory, an animal feed additive, and an animal feedstuff.

In one embodiment, the feedable accessory is one or more selected from the group consisting of a carrier, a diluent, an excipient, and a solvent.

In one embodiment, the animal feed additive is one or more selected from the group consisting of a nutritive feed additive, a general feed additive, and a medicated feed additive.

Compared with prior art, the present disclosure has the following beneficial effects:

The present disclosure has proved through animal breeding tests that, using the diphenylpropenone compounds, or stereoisomers, geometric isomers, tautomers, solvates or feed acceptable salts thereof as animal feed additives or animal feed additives can effectively increase animal weight, improve survival rate, and has a good effect of improving animal production performance.

DETAILED DESCRIPTION OF THE EMBODIMENTS

The use of the diphenylpropenone compounds of the present disclosure in the preparation of animal feed additives will be further described in detail below with reference to specific examples.

Certain embodiments of the present disclosure will be described in detail herein, the examples of which are illustrated by the accompanying structural formulas and chemical formulas. The present disclosure is intended to cover all substituted, modified and equivalent technical solutions, which are all included in the scope of the present disclosure as defined by the claims. In addition, certain technical features of the present disclosure are described separately in multiple independent embodiments for clarity, but they can also be provided in combination or any suitable sub-combination in a single example.

Compound:

The present disclosure relates to a use of a diphenylpropenone compound represented by Formula (I), or a stereoisomer, a geometric isomer, a tautomer, a solvate or a feed acceptable salt thereof in a preparation of feed additives or feeds.

Formula (I)

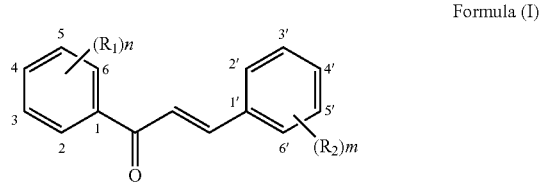

Wherein, $R_1$ represents any substituent group at the 1-position, 2-position, 3-position, 4-position or 5-position of the corresponding benzene ring, $R_2$ represents any substituent group at the 1'-position, 2'-position, 3'-position, 4'-position or 5'-position of the corresponding benzene ring, and n and m represent the number of groups substituted by $R_1$ and $R_2$ on the benzene ring, respectively. $R_1$ is OH, $C_1$-$C_{20}$ alkyl, $OC_1$-$C_{20}$ alkyl, C(=O)OH, C(=O)$OC_1$-$C_{20}$ alkyl or X, $R_2$ is OH, $C_1$-$C_{20}$ alkyl, $OC_1$-$C_{20}$ alkyl or X, n and m are integers from 0 to 5, and X is F, Cl, Br or I.

Generally, "substituted" means that one or more of the hydrogen atoms that can be substituted in the given structure are substituted by specific substituents. A substituted group may be formed by the substitution of one substituent group at each substitutable position of the group. When more than one position in the given structural formula can be substituted by one or more specific substituents, it may be same or differently substituted by the substituent groups at each position.

In the present disclosure, "$C_a$-$C_b$ alkyl" means a linear or branched saturated alkyl containing a to b carbon atoms, such as, methyl, ethyl, propyl, isopropyl, etc. For example, "$C_1$-$C_5$ alkyl" means a linear or branched saturated alkyl containing 1 to 5 carbon atoms.

In some embodiments, the numbers n and m of the substituent groups $R_1$ and $R_2$ in the diphenylpropenone represented by the Formula (I) and derivatives thereof are 0 simultaneously.

In some embodiments, $R_1$ in the diphenylpropenone represented by the Formula (I) and derivatives thereof is OH.

In some embodiments, $R_1$ in the diphenylpropenone represented by the Formula (I) and derivatives thereof is $OC_1$-$C_{20}$ alkyl.

In further embodiments, said $R_1$ is preferably $OC_1$-$C_5$ alkyl.

Optionally, said $R_1$ is $OC_1$-$C_5$ linear alkyl, specifically a methoxy group ($OCH_3$), an ethoxy group ($OCH_2CH_3$), a propoxy group ($O(CH_2)_2CH_3$), a butoxy group ($O(CH_2)_3CH_3$), or a pentyloxy group ($O(CH_2)_4CH_3$).

Further optionally, said $R_1$ is $OC_1$—$O_5$ branched alkyl, including but not limited to an isopropoxy group ($OCH_2(CH_3)_2$), and an isobutoxy group ($OC(CH_3)_3$).

In some embodiments, $R_1$ in the diphenylpropenone represented by the Formula (I) and derivatives thereof is $C_1$-$C_{20}$ alkyl.

In further embodiments, said $R_1$ is preferably $C_1$-$C_5$ alkyl.

Optionally, said $R_1$ is $C_1$-$C_5$ linear alkyl, specifically methyl ($CH_3$), ethyl ($CH_2CH_3$), propyl (($CH_2)_2CH_3$), butyl (($CH_2)_3CH_3$), or pentyl (($CH_2)_4CH_3$).

Further optionally, said $R_1$ is $C_1$-$C_5$ branched alkyl, including but not limited to isopropyl ($CH_2(CH_3)_2$), and isobutyl ($C(CH_3)_3$).

In some embodiments, $R_1$ in the diphenylpropenone represented by the Formula (I) and derivatives thereof is C(=O)OH or C(=O)$OC_1$-$C_{20}$ alkyl.

In further embodiments, said $R_1$ is preferably C(=O)OH or C(=O)$OC_1$-$C_5$ alkyl.

Optionally, when said $R_1$ is C(=O)$OC_1$-$C_5$ alkyl, it is preferably C(=O)$OC_1$-$C_5$ linear alkyl, specifically, C(=O)$OCH_3$, C(=O))$OCH_2CH_3$, C(=O)$O(CH_2)_2CH_3$, C(=O)$O(CH_2)_3CH_3$ or C(=O)$O(CH_2)_4CH_3$.

Optionally, when said $R_1$ is C(=O)$OC_1$-$C_5$ alkyl, it is preferably C(=O)$OC_1$-$C_5$ branched alkyl, including but not limited to C(=O)$OCH_2(CH_3)_2$, and C(=O)$OC(CH_3)_3$.

In some embodiments, $R_1$ in the diphenylpropenone represented by the Formula (I) and derivatives thereof is halogen X, specifically, F, Cl, Br or I.

In further embodiments, said $R_1$ is preferably Cl.

In some embodiments, $R_2$ in the diphenylpropenone represented by the Formula (I) and derivatives thereof is OH.

In some embodiments, $R_2$ in the diphenylpropenone represented by the Formula (I) and derivatives thereof is $OC_1$-$C_{20}$ alkyl.

In further embodiments, said $R_2$ is preferably $OC_1$-$C_5$ alkyl.

Optionally, said $R_2$ is $OC_1$-$C_5$ linear alkyl, specifically, a methoxy group ($OCH_3$), an ethoxy group ($OCH_2CH_3$), a propoxy group ($O(CH_2)_2CH_3$), a butoxy group ($O(CH_2)_3CH_3$), or a pentyloxy group ($O(CH_2)_4CH_3$).

Optionally, said $R_2$ is $OC_1$-$C_5$ branched alkyl, including but not limited to an isopropoxy group ($OCH_2(CH_3)_2$), and an isobutoxy group ($OC(CH_3)_3$).

In some embodiments, $R_2$ in the diphenylpropenone represented by the Formula (I) and derivatives thereof is $C_1$-$C_{20}$ alkyl.

In further embodiments, said $R_2$ is preferably $C_1$-$C_5$ alkyl.

Optionally, said $R_2$ is $C_1$-$C_5$ linear alkyl, specifically, methyl ($CH_3$), ethyl ($CH_2CH_3$), propyl ($(CH_2)_2CH_3$), butyl ($(CH_2)_3CH_3$), or pentyl ($(CH_2)_4CH_3$).

Further optionally, said $R_2$ is $C_1$-$C_5$ branched alkyl, including but not limited to isopropyl ($CH_2(CH_3)_2$), and isobutyl ($C(CH_3)_3$).

In some embodiments, $R_2$ in the diphenylpropenone represented by the Formula (I) and derivatives thereof is halogen X, specifically, F, Cl, Br or I.

In further embodiments, said $R_2$ is preferably Cl.

In some embodiments, the diphenylpropenone represented by the Formula (I) and derivatives thereof are polysubstituted derivatives of $R_1$ and/or $R_2$, and n and m are each selected from 1, 2, 3, 4, or 5.

Optionally, n and m are the same, and are selected from 1, 2, 3, 4, or 5.

Compound Preparation and Purification:

The preparation method of the diphenylpropenone represented by the Formula (I) and derivatives thereof in the present disclosure mainly involves Claisen-Schmidt condensation reaction. In the Claisen-Schmidt condensation reaction, the phenyl substituted derivative of acetophenone (abbreviated as AB) and the phenyl substituted derivative of benzaldehyde (abbreviated as BZ) are used as starting materials to perform an aldol condensation reaction under alkaline condition such as sodium hydroxide. The reaction process is as shown in Equation (II).

Equation (II)

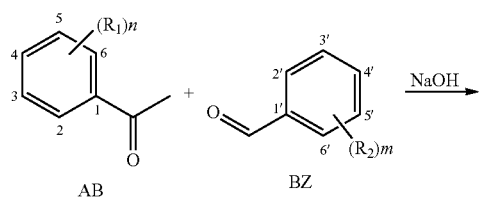

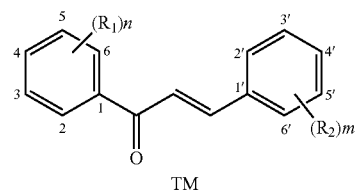

TM

To be clear, NaOH in Equation (II) represents sodium hydroxide.

In some technical solutions, the target material (TM) generated by the reaction process shown in the above Equation (II) has a configuration transformation of tautomer shown in the Equation (III) under suitable conditions.

Equation (III)

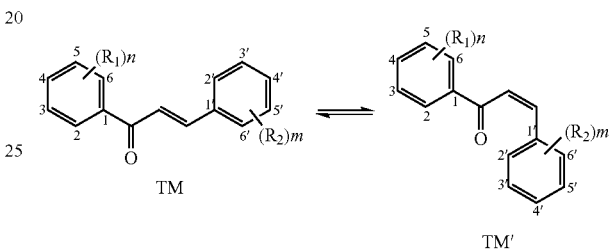

When the corresponding diphenylpropenone and derivatives thereof generated from the reaction of the involved reactive materials the phenyl substituted derivative of acetophenone (abbreviated as AB) and the phenyl substituted derivative of benzaldehyde have a rigid structure, the reaction substrate can generate different geometric isomer products during the reaction.

The aforementioned geometric isomer and tautomer are also included in the scope of implementation of the present disclosure.

The "geometric isomer" involved in the present disclosure refers to a compound having the same chemical structure but different arrangement of atoms or groups in space, including one of the stereoisomers, such as an enantiomer, a diastereomer, a conformational isomer, a geometric isomer, and an atropisomer, and the like. The "enantiomer" refers to two isomers of a compound that cannot be overlapped but are mirror images of each other. The "diastereomer" refers to a stereoisomer that has two or more chiral centers and whose molecules are not mirror images of each other, and has different physical properties, such as melting point, boiling point, spectral property, and reactivity. Diastereoisomer mixtures can be separated by high-resolution analysis operations such as electrophoresis or chromatography. The "tautomer" refers to constitutional isomers having different energies that can be converted into each other through a low energy barrier.

In some embodiments, the preparation process of the diphenylpropenone and derivatives thereof provided in the present disclosure also involves a separation, purification or recrystallization process of the reaction products. The reaction products can be obtained as crude products from the reaction system by a solvent removal method. In order to obtain solid substances with higher chemical purity and lower impurity content, the crude products are dissolved, crystallized or precipitated or recrystallized and separated in alcohol solvent, alcohol-water mixed solvent or other organic solvents that can be used for product recrystallization under suitable temperature, light and mechanical vibration conditions, to obtain diphenylpropenone and derivatives thereof with a certain crystal state. The diphenylpropenone and derivatives thereof with a certain crystal state are crystals of the diphenylpropenone and derivatives thereof or solvates of the diphenylpropenone and derivatives thereof.

The solvates of the diphenylpropenone and derivatives thereof can be selected from hydrates of the diphenylpropenone and derivatives thereof or ethanolates of the diphenylpropenone and derivatives thereof.

The "solvate" involved in the present disclosure refers to an eutectic association compound formed by binding chemically equivalent or non-chemically equivalent solvent molecules to the compound of the present disclosure through non-covalent intermolecular forces under external conditions and internal conditions during the contact between the compound of the present disclosure and the solvent molecules. Solvents for forming the solvates include, but are not limited to, solvents such as water, acetone, ethanol, methanol, dimethyl sulfoxide, ethyl acetate, acetic acid, and isopropanol, or the like. The "hydrate" refers to an association compound or crystal formed when the solvent molecule is water, i.e., a compound formed by binding the chemically equivalent or non-chemically equivalent water through the non-covalent intermolecular forces.

In order to obtain solid substances with higher chemical purity and lower impurity content, the preparation of the diphenylpropenone and derivatives thereof provided by the present disclosure may further involve a post-treatment by salting out method. The salting out method is a salt precipitation process of amino acid derivatives and corresponding organic base, inorganic base, organic acid or inorganic acid using the principle of acid-base neutralization method, acid-base coordination method or acid-base chelation method, to obtain feed acceptable salts. The inorganic acid includes, but is not limited to, hydrochloride, hydrobromide, phosphate, sulfate, nitrate or a combination thereof. The organic base includes, but is not limited to, ammonia or triethylamine. The inorganic base includes, but is not limited to, sodium hydroxide, potassium hydroxide, magnesium hydroxide, or calcium hydroxide.

The feed acceptable salts are salts formed by the diphenylpropenone and derivatives thereof of the present disclosure and an organic base, an inorganic base, an organic acid or an inorganic acid that is non-toxic to animals. The "feed acceptable" means that the substance or composition must be chemically or toxicologically suitable, and it is related to the feed to be formed or the farm animals eating it.

In some embodiments, the diphenylpropenone and derivatives thereof are ester derivatives, which forms a acid-base coordination salt and/or acid-base chelate salt with an inorganic acid or an organic acid in the salting-out precipitation process of post-treatment. The organic acid includes, but is not limited to, acetate, maleate, succinate, mandelate, fumarate, malonate, malate, 2-hydroxypropionate, pyruvate, oxalate, glycolate, salicylate, glucuronate, galactitolate, citrate, tartrate, aspartate, glutamate, benzoate, p-methylbenzoate, cinnamate, p-toluenesulfonate, benzenesulfonate, methanesulfonate, ethanesulfonate, triflate, or a combination thereof.

Use of the Diphenylpropenone Compound Involved in the Present Disclosure:

The diphenylpropenone compound or the geometric isomer, the tautomer, the solvate or the feed acceptable salt thereof provided by the present disclosure is used in the preparation of animal feed additives or animal feeds.

The "animal" involved in the present disclosure refers to a person or farm animal who cannot synthesize inorganic substances into organic substances, and can only use organic substances as foodstuff for life activities such as ingestion, digestion, absorption, respiration, circulation, excretion, sensation, movement, and breeding. The "farm animal" includes poultry, livestock, aquaculture animals and other animals that are artificial feeding and legally captured, including pets, such as cats and dogs. The term "livestock" is any one of, for example, a pig, cattle, horse, goat, sheep, deer and many useful rodents. The term "poultry" includes, for example, a chicken, duck, goose, quail, pigeon, and the like. The term "aquaculture animal" includes, for example, a fish, shrimp, turtle, amyda, and the like.

The diphenylpropenone compound, or the geometric isomer, the tautomer, the solvate or the feed acceptable salt thereof provided by the present disclosure is used to prepare non-nutritive additives for improving production performance of animals at various growth stages. The animal may be selected from livestock, poultry, aquaculture animal or pet at various growth stages.

Further, the livestock includes, but is not limited to a pig, cattle, sheep, horse, rabbit, mink or donkey, the poultry includes, but is not limited to a chicken, turkey, duck, goose, quail or pigeon, and the aquaculture animal includes, but is not limited to a fish, shrimp, turtle, crab, amyda, bullfrog, eel or loach, and the pet includes, but is not limited to a dog or cat of various subspecies.

In one embodiment, the diphenylpropenone compound, or the geometric isomer, the tautomer, the solvate or the feed acceptable salt thereof provided by the present disclosure is used to prepare feed additives for improving the production performance of pork pigs, which have an improvement effect on the average daily gain and feed conversion efficiency of pork pigs.

In another embodiment, the diphenylpropenone compound, or the geometric isomer, the tautomer, the solvate or the feed acceptable salt thereof provided by the present disclosure is used to prepare feed additives capable of significantly improving the production performance of broilers or layers.

In one embodiment, the diphenylpropenone compound, or the geometric isomer, the tautomer, the solvate or the feed acceptable salt thereof provided by the present disclosure is used to prepare feed additives for improving the production performance of fishes.

The feed acceptable salt of the diphenylpropenone compound provided by the present disclosure used in the preparation of animal feed additives is a metal ion salt.

Optionally, the feed acceptable salt of the diphenylpropenone compound is a metal ion salt of the diphenylpropenone compound having structure represented by the Formula (I).

Further, when the diphenylpropenone compound having structure represented by the Formula (I) contains active H, the metal ion salt is a salt obtained by exchanging the active H of the diphenylpropenone compound with metal ions that meets the preparation requirements of feed additives or feeds.

Specifically, the metal ion is selected from a monovalent metal ion, a divalent metal ion or a trivalent metal ion.

In some embodiments, the monovalent metal ion is sodium ion (Na(I)), potassium ion (K(I)) or lithium ion (Li(I)).

In some embodiments, the divalent metal ion is calcium ion Ca(II), magnesium ion Mg(II), copper ion Cu(II), zinc ion Zn(II), ferrous ion Fe(II), manganese ion Mn(II), cobalt ion Co(II) or nickel ion Ni(II).

In one embodiment, the metal ion salt of the diphenylpropenone compound used in the preparation of the animal feed additives is a zinc ion salt, and the animal feed additive is an organic zinc agent for animals as an alternative to a high-level inorganic zinc.

In one embodiment, the metal ion salt of the diphenylpropenone compound used in the preparation of the animal feed additives is a copper ion salt, and the animal feed additive is an organic copper agent for animals as an alternative to a high-level inorganic copper.

In one embodiment, the metal ion salt of the diphenylpropenone compound used in the preparation of the animal feed additives is an iron ion salt, and the animal feed additive is an iron supplement for animals.

In some embodiments, the trivalent metal ion is aluminum ion Al(III), chromium ion Cr(III) or iron ion Fe(III).

Feed Composition Involved in the Present Disclosure:

The feed composition comprises the diphenylpropenone compound represented by General Formula (I), or the stereoisomer, the geometric isomer, the tautomer, the solvate or the feed acceptable salt thereof, and one or more of a feedable accessory, an animal feed additive, and an animal feedstuff.

Further, the feedable accessory is one or more selected from the group consisting of a carrier, a diluent, an excipient, and a solvent.

The "feed" involved in the present disclosure refers to an industrially processed and manufactured product for animal consumption.

The "composition" involved in the present disclosure refers to a compound collective comprising one or more compounds as effective ingredients.

The "comprising" mentioned in the present disclosure is an open-type expression, which includes the contents explicitly indicated in the present disclosure, but does not exclude other contents.

The "carrier" involved in the present disclosure refers to a feedable substance capable of carrying active ingredients, improving its dispersibility, and having good chemical stability and adsorption, including an organic carrier and an inorganic carrier. The organic carrier is a material containing a lot of crude fiber, including but not limited to corn flour, corncob flour, wheat bran, rice hull flour, defatted rice bran, rice bran and hull, corn stalk flour, peanut husk flour, and the like. The inorganic carrier is a mineral, mainly divided into calcium salts and silicon oxides, which is used for the production of trace element premix, including but not limited to calcium carbonate, silicate, vermiculite, zeolite, sepiolite, and the like.

The "diluent" involved in the present disclosure refers to a substance that evenly distributes the additive raw materials in the material, dilutes the high-concentration additive raw materials into a low-concentration premixing agent or premix, which can separate trace components from each other and reduce the interreaction between the active ingredients to increase the stability of the active ingredients without affecting the physical and chemical properties of related substances, including an organic diluent or an inorganic diluent. The organic diluent includes, but is not limited to, corn flour, degerminated corn flour, dextrose (glucose), sucrose, manna-croup with bran, fried soybean flour, middling flour, corn gluten meal, and the like. The inorganic diluent includes, but is not limited to, limestone, calcium dihydrogen phosphate, shell powder, kaolin (porcellanite), table salt and sodium sulfate.

The excipient is a wetting agent that induces the inherent viscosity of a substance, a binder that binds substances together, a disintegrant that breaks the entire sheet of a substance into many fine particles, a retention aid that reduces friction between particles or an antiblock agent that prevents material adhesion, including, but being not limited to, magnesium stearate, talc, vegetable oil, magnesium lauryl sulfate, starch, starch slurry, water, inorganic salt, dextrin, powdered sugar, and the like.

The "solvent" involved in the present disclosure refers to a solvent required to dissolve or disperse solids, including, but being not limited to, water, ethanol, glycerin, and the like.

The animal feed additive is one or more of a nutritive feed additive, a general feed additive or a medicated feed additive.

The nutritive feed additive refers to a small or trace substance that is added to compound feeds to balance feed nutrients, improve feed utilization, and directly exert nutritional effects on animals, including an amino acid, an amino acid salt and analogs thereof, a vitamin and vitamins, a mineral element and complexes (chelates) thereof, a microbial enzyme preparation or a non-protein nitrogen.

The general feed additive is also called non-nutritive additive, which refers to some non-nutritive substances that are added to feed to improve feed utilization, ensure the quality of feed, and are beneficial to the health or metabolism of animals, including growth promoter, insect repellent and health care agent, flavoring and attractant agent, feed texturizer, feed modulator, feed storage agent and Chinese herbal medicine additive.

More specifically, the non-nutritive additive is a growth promoter, including, but being not limited to, butyric acid, calcium butyrate, sodium butyrate, tannic acid, p-thymol, p-thymol ester, p-thymol salt, 2-hydroxybenzoic acid, β-acid, β-acid ester, β-acid salt, hexahydro-β-acid, hexahydro-β-acid ester, hexahydro-β-acid salt, benzoic acid or calcium benzoate, zinc oxide, zinc sulfate, and zinc chloride.

In one embodiment, the non-nutritive additive is calcium butyrate.

In another embodiment, the non-nutritive additive is tannic acid.

The medicated feed additive includes, but is not limited to, premixed materials for veterinary drugs that have the functions of preventing animal diseases and promoting animal growth and can be added to feeds for a long time and be incorporated with carriers or diluents.

Specifically, the medicated feed additive is a feed antibiotic, including, but being not limited to, polymyxin, salinomycin, avilamycin, bacitracin, virginiamycin, nosiheptide, flavomycin, enramycin, kitasamycin, olaquindox, oxytetracycline or aureomycin.

The animal feedstuff is a feed substance such as grains and processed products thereof, oil seeds and processed products thereof, legumes and processed products thereof, tubers, tuberous roots and processed products thereof, other seeds and fruit products and processed products thereof, forage grass, coarse fodder and processed products thereof, other plants, algae and processed products thereof, dairy products and by-products thereof, terrestrial animal products and by-products thereof, fishes, other aquatic organisms and by-products thereof, minerals, microbial fermentation products and by-products, and other feedstuffs.

Use of the Feed Composition:

The present disclosure relates to a use of the abovementioned feed composition comprising the diphenylpropenone compound, or the geometric isomer, the tautomer, the solvate or the feed acceptable salt thereof.

In some embodiments, the feed composition comprising the diphenylpropenone compound, or the geometric isomer, the tautomer, the solvate or the feed acceptable salt thereof is used in the preparation of animal feed additives.

The animal feed additives prepared by using the feed composition comprising the diphenylpropenone compound, or the geometric isomer, the tautomer, the solvate or the feed acceptable salt thereof are livestock feed additives, poultry feed additives, aquaculture animal feed additives or pet feed additives.

Specifically, the feed composition comprising the diphenylpropenone compound, or the geometric isomer, the tautomer, the solvate or the feed acceptable salt thereof is used to prepare the livestock feed additives. The livestock includes, but is not limited to, a pig, cattle, sheep, horse, rabbit, mink, and the like at various growth stages.

Specifically, the feed composition comprising the diphenylpropenone compound, or the geometric isomer, the tautomer, the solvate or the feed acceptable salt thereof is used to prepare the poultry feed additives. The livestock includes, but is not limited to, a chicken, duck, goose, pigeon, and the like at various growth stages.

Specifically, the feed composition comprising the diphenylpropenone compound, or the geometric isomer, the tautomer, the solvate or the feed acceptable salt thereof is used to prepare the aquaculture animal feed additives. The aquaculture animal includes, but is not limited to, a fish, shrimp, crab, amyda, eel, and the like at various growth stages.

Specifically, the feed composition comprising the diphenylpropenone compound, or the geometric isomer, the tautomer, the solvate or the feed acceptable salt thereof is used to prepare the pet feed additives. The pet includes, but is not limited to, an artificial feeding dog or cat.

In some embodiments, the animal feed additives prepared with the composition comprising the diphenylpropenone compound, or the geometric isomer, the tautomer, the solvate or the feed acceptable salt thereof are premix, multi-premix, water aquas or granules.

In some embodiments, the feed composition comprising the diphenylpropenone compound, or the geometric isomer, the tautomer, the solvate or the feed acceptable salt thereof is used in the preparation of animal feeds.

The animal feed additives prepared by using the feed composition comprising the diphenylpropenone compound, or the geometric isomer, the tautomer, the solvate or the feed acceptable salt thereof are livestock feeds, poultry feeds, aquaculture animal feeds or pet feeds.

Specifically, the feed composition comprising the diphenylpropenone compound, or the geometric isomer, the tautomer, the solvate or the feed acceptable salt thereof is used to prepare the livestock feeds. The livestock includes, but is not limited to, a pig, cattle, sheep, horse, rabbit, mink, and the like at various growth stages.

Specifically, the feed composition comprising the diphenylpropenone compound, or the geometric isomer, the tautomer, the solvate or the feed acceptable salt thereof is used to prepare the poultry feeds. The livestock includes, but is not limited to, a chicken, duck, goose, pigeon, and the like at various growth stages.

Specifically, the feed composition comprising the diphenylpropenone compound, or the geometric isomer, the tautomer, the solvate or the feed acceptable salt thereof is used to prepare the aquaculture animal feeds. The aquaculture animal includes, but is not limited to, a fish, shrimp, crab, amyda, eel, and the like at various growth stages.

Specifically, the feed composition comprising the diphenylpropenone compound, or the geometric isomer, the tautomer, the solvate or the feed acceptable salt thereof is used to prepare the pet feeds. The pet includes, but is not limited to, an artificial feeding dog or cat.

In some embodiments, the feeds prepared by using the feed composition comprising the diphenylpropenone compound, or the geometric isomer, the tautomer, the solvate or the feed acceptable salt thereof are single feeds, concentrated feeds, formula feeds, multi-premixes or concentrate supplements.

Specifically, the compound feed is a complete formula feed.

Method for Improving the Production Performance of Farm Animals:

In some feeding embodiments, the fanner feeds animals with the feed additives comprising the diphenylpropenone compound, or the geometric isomer, the tautomer, the solvate or the feed acceptable salt thereof along with feeds, which can significantly improve the production performance of the animals.

In some embodiments, the feed additives are premix, multi-premix, granules or water aquas, which are mixed with animal feeds for feeding animals.

The animal is a livestock, poultry, aquaculture animal or pet.

Specifically, the livestock includes, but is not limited to, a pig, cattle, sheep, horse, rabbit, mink, and the like at various growth stages. The poultry includes, but is not limited to, a chicken, duck, goose, pigeon, and the like at various growth stages. The aquaculture animal includes, but is not limited to, a fish, shrimp, crab, amyda, eel, and the like at various growth stages. And, the pet includes, but not limited to, an artificial feeding dog or cat.

In one embodiment, the farmer feeds weaned pigs with the feed additives comprising the diphenylpropenone compound, or the geometric isomer, the tautomer, the solvate or the feed acceptable salt thereof along with feeds, which significantly increases the weight gain rate for average daily gain and the feed conversion efficiency of the weaned pigs.

In one embodiment, the farmer feeds broilers with the feed additives comprising the diphenylpropenone compound, or the geometric isomer, the tautomer, the solvate or the feed acceptable salt thereof along with feeds, which significantly reduces the feed conversion ratio of broilers and increases the feed conversion efficiency.

In one embodiment, the fanner feeds fishes with the feed additives comprising the diphenylpropenone compound, or the geometric isomer, the tautomer, the solvate or the feed acceptable salt thereof along with feeds.

In one embodiment, the farmer feeds puppies with the feed additives comprising the diphenylpropenone compound, or the geometric isomer, the tautomer, the solvate or the feed acceptable salt thereof along with feeds.

In other feeding embodiments, the farmer feeds animals with the feed compositions comprising the diphenylpropenone compound, or the geometric isomer, the tautomer, the solvate or the feed acceptable salt thereof, which can significantly improve the production performance of the animals.

Optionally, the feed composition is a feed additive premix, feed additive multi-premix, granule or water aqua, which is fed to animals along with feeds.

In one embodiment, the feed composition is a feed additive premix.

In one embodiment, the feed composition is a feed additive multi-premix.

Optionally, the feed composition is a concentrated feed, a formula feed, a multi-premix or a concentrate supplement, which is directly fed to animals as an animal feed.

In one embodiment, the feed composition is a complete formula feed.

Breeding Test:

The diphenylpropenone and derivatives thereof involved in the breeding test are shown in Table 1.

TABLE 1

List of the diphenylpropenone and derivatives thereof

| Compound No. | R1 | R2 |
|---|---|---|
| Compound 1 | n = 0 | m = 0 |
| Compound 2 | n = 0 | 4'-CH$_3$ |
| Compound 3 | 3-OH | m = 0 |
| Compound 4 | 2-OH | 3'-CH$_3$ |
| Compound 5 | 3-OH, 5-OH | 3'-CH$_3$ |
| Compound 6 | 4-COOH | m = 0 |
| Compound 7 | 4-OCH$_3$ | 4'-OCH$_3$ |
| Compound 8 | 4-O(CH$_2$)$_4$CH$_3$ | 4'-O(CH$_2$)$_4$CH$_3$ |
| Compound 9 | 4-Cl | 4'-Cl |

Example B1. Effect of the Diphenylpropenone and Derivatives Thereof on the Production Performance of Pork Pigs 300 head of 65-day-old "duroc×landrace×Large Yorkshire" three-way cross lean-type piglets with similar body weights were randomly divided into 10 treatment groups, each group having 3 repetitions, and each repetition having 10 piglets, half male and half female. The pigpens and appliances were sterilized before testing. During the test, the piglets were fed in separate pens under the same feeding and management condition in the same pigpen. During the test, the test pigs ate and drank freely, and were fed twice a day. Each test group is control group and test groups II to X, respectively. Wherein, the control group was fed with a basal diet only, and the test groups II to X were fed with diets that were supplemented with 500 ppm of different diphenylpropenones and derivatives thereof on the basis of the basal diet, as shown in Table 2. During the entire feeding process, no additional antioxidant components or growth promoters were added for each test group. The test period is 28 days, with each repetition as a unit, the pigs were weighed at the age of 93 days after not stopping water but stopping feeding for 12 hours to calculate the average daily feed intake (ADFI, g/d*head), average daily gain (ADG, g/d*head) and feed conversion ratio (FCR) for each test group. The calculation formulas are as follows:

Average daily feed intake=(total amount of feeds-remaining amount of feeds)/(test days×number of pigs per repetition);

Average daily gain=(average weight at the end of the test-average weight at the beginning of the test)/test days;

Feed conversion ratio=average daily feed intake/average daily gain.

The results of the test are shown in Table 2. The effects of the test samples used in this experiment on the production performance of the test pigs were evaluated in terms of three aspects of feed intake, weight gain and feed conversion efficiency. It can be seen from the results that, the test samples have no significant effect on the feed intake of the test pigs. However, the average daily gain of each test group is increased to varying degrees regardless of whether the food intake is less than that of the control group, wherein, it is the most significant for the test group VII. The feed conversion ratio is decreased by about 3% to 5% for each test group compared with the control group.

TABLE 2

Results of the effect of the diphenylpropenone and derivatives thereof on the production performance of piglets

| Test group | Test sample | ADFI (g/d*head) | ADG (g/d*head) | FCR |
|---|---|---|---|---|
| Group I | — | 1601 | 586 | 2.733 |
| Group II | Compound 1 | 1584 | 596 | 2.658 |
| Group III | Compound 2 | 1597 | 605 | 2.64 |
| Group IV | Compound 3 | 1622 | 621 | 2.613 |
| Group V | Compound 4 | 1639 | 626 | 2.619 |
| Group VI | Compound 5 | 1641 | 632 | 2.596 |
| Group VII | Compound 6 | 1635 | 632 | 2.588 |
| Group VIII | Compound 7 | 1576 | 598 | 2.636 |
| Group IX | Compound 8 | 1608 | 612 | 2.627 |
| Group X | Compound 9 | 1585 | 607 | 2.611 |

Example B2. Effect of the Diphenylpropenone and Derivatives Thereof on the Production Performance of Broilers A single-factor random design was adopted for the test. 600 of one-day-old Chinese three-yellow-feather broilers with similar weights having an average weight of 50 g were randomly divided into 10 treatment groups, each group having 3 repetitions, half male and half female, and each repetition with 20 Chinese three-yellow-feather broilers. The henhouse and appliances were sterilized before testing. During the test, the cage rearing was carried out in the same henhouse under the same feeding and management condition. The basal diet is mainly a corn-soybean meal, and no additional antioxidant components or growth promoters were added during the entire feeding process. Each test group is a control group and test groups I to X, respectively. Wherein, test group I is the control group fed with the basal diet only, and the test groups I to X were fed with diets that were added with 350 ppm of different diphenylpropenones and derivatives thereof on the basis of the basal diet. The grouping is shown in Table 3. The test period was 20 days in total. The test broilers were free to drink and eat, and were fed twice a day, with each repetition as a unit, the test broilers were weighed at the age of 21 days (stopping feeding for 12 hours, without stopping water) to count the consumption of the test broilers, calculate the average daily feed intake (ADFI, g/d*number of broilers), average daily gain (ADG, g/d*number of broilers) and feed conversion ratio (FCR) of each group of test broilers. The calculation formulas are as follows:

Feed conversion ratio (FCR)=average daily feed intake/average daily gain.

The test results are shown in Table 3. From the results, it can be seen that the test samples have no significant effect on the feed intake of the test broilers. Regarding the effect on the average daily gain, compared with the control group, the average daily gain of each test group is increased by 4.6%~19.5% except for the test group II. The test samples have an improvement effect on the feed conversion ratio of each test group, with overall decrease by about 1.3% to 7.2%.

TABLE 3

Study of the application effects of the diphenylpropenone and derivatives thereof on broiler feeds

| | Test sample | ADFI (g/d*number of broilers) | ADG (g/d*number of broilers) | FCR |
|---|---|---|---|---|
| Group I | — | 30.3 | 12.8 | 2.36 |
| Group II | Compound 1 | 30.1 | 12.9 | 2.33 |
| Group III | Compound 2 | 32.4 | 14.1 | 2.30 |
| Group IV | Compound 3 | 33.8 | 15.3 | 2.21 |
| Group V | Compound 4 | 29.5 | 13.4 | 2.2 |
| Group VI | Compound 5 | 30.0 | 13.6 | 2.2 |
| Group VII | Compound 6 | 31.1 | 14.2 | 2.19 |
| Group VIII | Compound 7 | 31.7 | 13.9 | 2.28 |
| Group IX | Compound 8 | 30.9 | 13.6 | 2.27 |
| Group X | Compound 9 | 32.3 | 14.5 | 2.22 |

Example B4. Use of the Diphenylpropenone and Derivatives Thereof in Fish Feeds

The test fish used was a grass carp, and the test was carried out in an aquaculture farm in a testing ground of Guangzhou Insighter Biotechnology Co., Ltd. Healthy and lively grass carps with similar size were seeded and raised in a large net cage for 4 weeks before formal breeding test. The experimental system was a small floating net cage. Both of the small net cage and the temporary net cage were placed in a 3500 m² pond in the testing ground, the pond had a depth of about 1.5 m, and the pond water was fully aerated underlying water. During the test, 400 grass carps that were hungry for 1 day were randomly divided into 10 groups, each group having 4 repetitions, and each repetition having 10 grass carps. After weighing at a whole, they were randomly placed in 40 net cages and fed with different test feeds. The feeds for the test were self-prepared, and 250 ppm of different diphenylpropenones and derivatives thereof were added into the basic feeds for different test groups. The grouping is shown in Table 4. Artificial feed restriction was adopted in the test, and the feeding amount was adjusted once a week. The feeding level (based on initial body weight) of the two groups was exactly the same, feeding twice a day (7:30 and 15:00), with a total of 580 g. The test lasted for 8 weeks.
Parameter Calculation:

Weight gain rate (%)=(average final weight-average initial weight)/average initial weight*100

Feed coefficient=580/(average final weight-average initial weight)

The growth-promoting test results of different diphenylpropenones and derivatives thereof on fish are shown in Table 4. The results show that, compared with the control group, the test group added with the diphenylpropenones and derivatives thereof showed no significant improvement on weight gain and feed conversion efficiency, but the survival rate of the test fish in each test group was significantly higher than that of the control group.

TABLE 4

Grouping and results of application test of the diphenylpropenones and derivatives thereof in grass carp feeds

| | Test sample | Average initial weight (g) | Average final weight (g) | Weight gain rate (%) | Feed coefficient | Survival rate (%) |
|---|---|---|---|---|---|---|
| Group I | — | 400 | 705 | 76.32 | 1.90 | 68 |
| Group II | Compound 1 | 405 | 714 | 76.18 | 1.88 | 81 |
| Group III | Compound 2 | 411 | 718 | 74.67 | 1.89 | 83 |
| Group IV | Compound 3 | 392 | 706 | 79.98 | 1.85 | 89 |
| Group V | Compound 4 | 403 | 715 | 77.38 | 1.86 | 90 |
| Group VI | Compound 5 | 398 | 717 | 80.07 | 1.82 | 96 |
| Group VII | Compound 6 | 401 | 711 | 77.35 | 1.87 | 90 |
| Group VIII | Compound 7 | 397 | 711 | 78.97 | 1.85 | 88 |
| Group IX | Compound 8 | 409 | 724 | 77.07 | 1.84 | 87 |
| Group X | Compound 9 | 733 | 733 | 77.59 | 1.81 | 92 |

Each of the technical features of the above-mentioned embodiments may be combined arbitrarily. To simplify the description, not all the possible combinations of each technical feature in the above embodiments are described. However, all of the combinations of these technical features should be considered as within the scope of this disclosure, as long as such combinations do not contradict with each other.

The above-mentioned embodiments are merely illustrative of several embodiments of the present disclosure, which are described specifically and in detail, but it cannot be understood to limit the scope of the present disclosure. It should be noted that, for those ordinary skilled in the art, several variations and improvements may be made without departing from the concept of the present disclosure, and all of which are within the protection scope of the present disclosure. Therefore, the protection scope of the present disclosure shall be defined by the appended claims.

What is claimed is:

1. A method of achieving improved feed conversion efficiency and/or weight gain in an animal, the method comprising administering an animal feed additive to the animal, wherein the animal feed additive comprises a diphenylpropenone compound represented by General Formula (I), or a stereoisomer, a geometric isomer, a tautomer, a solvate or a feed acceptable salt thereof,

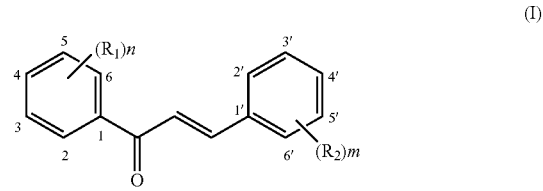

wherein, $R_1$ is each selected from OH, $C_1$-$C_{20}$ alkyl, $OC_1$-$C_{20}$ alkyl, $C(=O)OH$, $C(=O)OC_1$-$C_{20}$ alkyl or X; $R_2$ is each selected from OH, $C_1$-$C_{20}$ alkyl, $OC_1$-$C_{20}$ alkyl or X; n and m are integers from 0 to 2, and X is F, Cl, Br or I.

2. The method according to claim 1, wherein $R_1$ is each selected from OH, $OC_1$-$C_5$ alkyl, $C_1$-$C_5$ alkyl, $C(=O)OH$ or $C(=O)OC_1$-$C_5$ alkyl, F, Cl or Br.

3. The method according to claim 2, wherein $R_1$ is each optionally selected from OH, $C(=O)OH$, $OC_1$-$C_5$ alkyl or Cl.

4. The method according to claim 1, wherein $R_2$ is each selected from OH, $OC_1$-$C_5$ alkyl, $C_1$-$C_5$ alkyl, F, Cl or Br.

5. The method according to claim 4, wherein $R_2$ is each selected from $C_1$-$C_5$ alkyl, $OC_1$-$C_5$ alkyl or Cl.

6. The method according to claim 1, wherein, n≠0.

7. The method according to claim 6, wherein $R_1$ is each selected from OH, C(=O)OH or Cl; $R_2$ is each optionally selected from $C_1$-$C_5$ alkyl or Cl.

8. The method according to claim 1, wherein the diphenylpropenone compound is selected from the group consisting of following compounds:

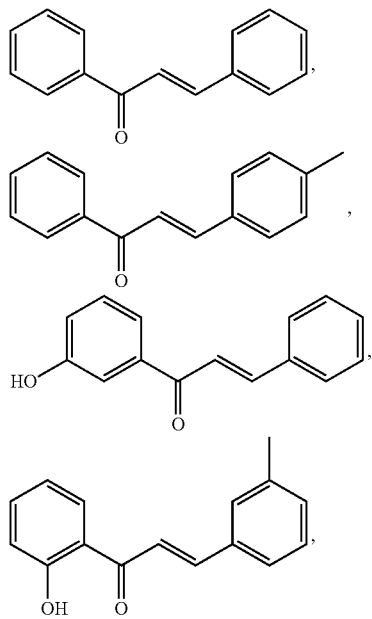

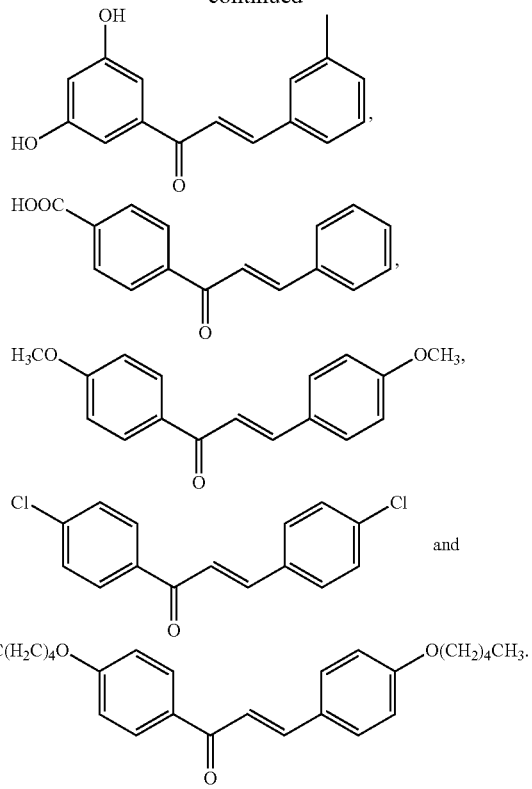

9. The method feed composition according to claim 1, wherein the animal feed additive further comprises one or more selected from the group consisting of a nutritive feed additive, a general feed additive, and a medicated feed additive.

* * * * *